US006787149B1

(12) United States Patent
El Khoury et al.

(10) Patent No.: US 6,787,149 B1
(45) Date of Patent: *Sep. 7, 2004

(54) TOPICAL APPLICATION OF OPIOID ANALGESIC DRUGS SUCH AS MORPHINE

(75) Inventors: George F. El Khoury, Long Beach, CA (US); Christoph Stein, Baltimore, MD (US)

(73) Assignee: El Khoury and Stein Ltd., Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/319,735

(22) PCT Filed: Dec. 12, 1996

(86) PCT No.: PCT/US96/19618

§ 371 (c)(1),
(2), (4) Date: Jan. 10, 2000

(87) PCT Pub. No.: WO98/25614

PCT Pub. Date: Jun. 18, 1998

(51) Int. Cl.[7] .......................... A61F 13/00; A61K 9/00; A61K 9/06; A61K 9/12
(52) U.S. Cl. ................... 424/434; 424/45; 424/449; 424/401; 514/282; 514/944
(58) Field of Search ................... 424/401, 434, 424/449, 45; 514/282, 944

(56) References Cited

U.S. PATENT DOCUMENTS 5,411,738 A   5/1995   Hind
5,866,143 A * 2/1999   Elkhoury .................... 424/401
5,919,473 A * 7/1999   Elkhoury .................... 424/422
6,011,022 A * 1/2000   ElKhoury .................... 514/78

FOREIGN PATENT DOCUMENTS

EP        0 704 206 A1      9/1995
GB        2 287 404 A       10/1994
WO        PCT/US96/19618    12/1996

OTHER PUBLICATIONS

European Search Report for Appl. No. EP 96 94 4286 Completed Jul. 11, 2000.
Tennant et al., "Topical Morphine for Peripheral Pain," Letters to the Editor, The Lancet, vol. 342, 1993, pp. 1047–1048.
Khoury, G.F. et al., "Intraarticular Morphine, Bupivacaine, and Morphine/Bupivacaine for Pain Control After Knee Videoarthroscopy," Anesthesiology, vol. 77, No. 263, 1992, pp. 236–266.
C. Stein et al., "Fentanyl Upon Nociception in Inflamed Tissue of the Rat," Neuroscience Letters, vol. 84, 1988, pp. 225–228.

* cited by examiner

Primary Examiner—Thurman K. Page
Assistant Examiner—Rachel M. Bennett
(74) Attorney, Agent, or Firm—Millen, White, Zelano & Branigan, P.C.

(57) ABSTRACT

The invention is directed to methods and pharmaceutical compositions for the topical administration of opioid analgesic drugs such as morphine. In particular, the invention relates to topical administration of an opioid analgesic agent, e.g., morphine sulfate, to produce a localized analgesic effect in inflamed skin or mucosal tissue, and without a transdermal or transmucosal migration of opioid agent, e.g., into the systemic circulation.

20 Claims, 1 Drawing Sheet

TOPICAL APPLICATION OF OPIOID ANALGESIC DRUGS SUCH AS MORPHINE

This application is a 371 of PCT/US96/19618 filed Dec. 12, 1996.

BACKGROUND OF THE INVENTION

Morphine is the prototype of the class of opioid analgesic drugs which exert their effects by activating opioid receptors within the brain. When morphine is referred to individually in this application, this reference is meant to encompass other opioid drugs and is not meant to be morphine exclusively. Historically, narcotics have been used since the 18th century in the forms of oral or injectable morphine or opium in order to accomplish pain relief. Morphine is considered to be unsurpassed as an analgesic for severe pain.

Unfortunately, morphine and other opioid drugs have a number of severe side effects which hamper their wide spread use and acceptance by both physicians and patients. These side effects include: addiction, nausea, inhibition of breathing, somnolence and dysphoria, all of which are mediated by morphine's action within the brain. It is still the current belief that narcotics ingested or injected will cross to the blood stream and from there go to the brain where there are morphine receptors. At that time, the narcotics are believed to attach to these morphine receptors and create a dullness of the pain but with all of the side effects described above. Of course, the worst potential effect is the addiction that can occur if the morphine is used beyond a few days or weeks on a continuous basis.

Because of the fear of addiction, the use of morphine as an analgesic has been restricted. In addition, major research efforts have been directed toward the development of morphine-like drugs that act within the brain but are devoid of the side effects. The market for these other drugs has never fully materialized because these drugs were not perceived as having the same analgesic properties of morphine and because typically these drugs were not produced to be both available in oral and injectable formats.

In the past ten years, the intraspinal method of treating pain has been developed tremendously but, as more extensive use was made of this technique, a number of serious problems developed. The first problem is that the intraspinal method of treatment requires a spinal tap which of course necessitates the use of a needle to the spinal cord. The second problem results from the first in that if it is necessary to use the intraspinal method over a period of time, such as two or three weeks, medication must be injected into the spine for this period of time and the continuous needle sticks into the spine has potential hazards. Further, if it is necessary to use the intraspinal method over time, even though the dosage is substantially less compared to oral or intravenous dosages, there is still a high potential for addiction and with such addiction the resultant problems of withdrawal and its associated side effects.

Although intraspinal application of narcotics is still used to alleviate pain after surgery, this technique has the limitations with the potential for addiction as described above. In addition, it has been determined that with frail patients there is the risk that the patient can stop breathing and there have been a number of cases of respiratory arrest after the administration of narcotics using the intraspinal technique. Further, the intraspinal technique of administering narcotics creates difficulty with male patients and especially with elderly male patients in that there can be problems with urination and with consequent problems of urine retention. Finally, this intraspinal technique produces a problem of itching and the sequences of continuous itching can be debilitating.

In more recent studies it was discovered that opioid receptors may also be located in other peripheral tissues. This was reported in Stein, C. et al., Peripheral effect of fentanyl upon nociception in inflamed tissue of the rat. Neurosci. Lett. 84:225–228 (1988), and in Stein, C. et al., Antinociceptive effects of mu- and kappa-agonists in inflammation are enhanced by a peripheral opioid receptor-specific mechanism of action. Eur. J. Pharmacol. 155:255–264 (1988). Subsequently, animal experiments were performed in Dr. Stein's laboratory characterizing peripheral opioid receptors and their activation by morphine and other opioid drugs. This was reviewed in Stein, C., Peripheral mechanisms of opioid analgesia. Anesth. Analg. 76:182–191 (1993), and in Stein, C., Lehrgerger, K., Yassouridis, A., Khoury, G.: Opioids as novel intraarticular agents in arthritis. In: Progress in Pain Research and Management, Fields, H. L., Liebeskind, J. C., eds., 1:289–296, IASP Press, Seattle, (1994). A most important determination from these various studies is that the doses of the drugs required to produce analgesia in the peripheral tissues are extremely small and therefore devoid of the above mentioned side effects produced by dosages sufficient to operate on the brain.

In addition, it was determined that the endogenous ligands of peripheral opioid receptors (endorphins, the body's own pain killers) are located within the inflamed tissue. It was also determined that the endorphins can produce intrinsic analgesia within peripheral tissues both in animals and in humans (Stein (1993), ibid.). It was further noted that the peripheral opioid effects were more pronounced in inflamed than in non-inflamed tissues.

An anecdotal preliminary study reported an attempt to transdermally locally administer 1–3 mg of morphine to the backs of patients who had undergone failed back operations, primarily using mechanical methods of enhancing skin penetration and absorption of the morphine (ultrasound, massage, heat) as well as by the use of the occlusive topical vehicle Aquaphor (F. Tennant et al., Topical morphine for peripheral pain. Lancet 342:1047–1048 (1993). Some improvement in pain relief was noted, and the authors speculated that it was due to binding of the morphine to peripheral opioid receptors in inflamed (presumably myofascial) tissue directly under the skin to which the morphine was applied, and absence of morphine in the systemic circulation was claimed. This result is scientifically questionable, however, based on the data of the present invention: there had to be sufficient transdermal transport to carry the morphine completely through the skin and into the underlying inflamed myofascial tissues, which would almost certainly result in a detectible amount of morphine being carried in the systemic circulation. Alternatively, it is possible that the pain relief noted was not reproducible. It is notable that no further reports of this type of administration have been reported since, either by that group or any others.

None of these reports discussed the possibility that pain relief could be topically induced in inflamed skin, nor was it even known whether peripheral opioid receptors are present in human skin.

Severe pain caused or accompanied by inflammation in skin is a particularly intractable problem, because the underlying reasons for it tend to be both long-term and yet not inherently life-threatening, e.g., shingles and various kinds of burns, both of militate against the chronic systemic use of opioid agents. Therefore, it would be a great benefit to be able to induce effective opioid analgesia in such cases without the negative effects of systemic opioid administration.

SUMMARY OF THE INVENTION

This invention provides a method of inducing analgesia in inflamed skin or mucosal tissue, comprising topically administering to a patient in need of such treatment a topically effective amount of an opioid analgesic agent, which amount is systemically ineffective for induction of analgesia, admixed with a pharmaceutically acceptable excipient for topical administration, preferably whereby effective analgesia in the inflamed skin or mucosal tissue is induced in the substantial absence of transdermal or transmucosal delivery of the opioid analgesic agent.

A further object of the invention is to provide a pharmaceutical composition comprising an admixture of an opioid analgesic agent and a pharmaceutically acceptable excipient for topical administration to inflamed skin or mucosal tissue, wherein a unit dosage amount of the admixture contains a systemically ineffective amount of the opioid analgesic agent, and the excipient does not enhance transdermal or transmucosal transmission of the opioid analgesic agent, with the proviso that, when the admixture is a liquid, it further comprises a component that is pharmaceutically unacceptable for parenteral administration.

Upon further study of the specification and claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

As a specific example, 90 mg of morphine sulfate may be diluted in 120 cc of saline to form the spray 12. The morphine sulfate is initially provided as a solution of 10 mg/cc, whereby the final spray solution contains 90 mg in a total of 129 cc. Thus, the final concentration of morphine in the spray is 0.69 mg/cc. The specific application may result in approximately 2 to 3 mg of morphine in solution to cover approximately a 6×6 square inch area.

Figure 2:
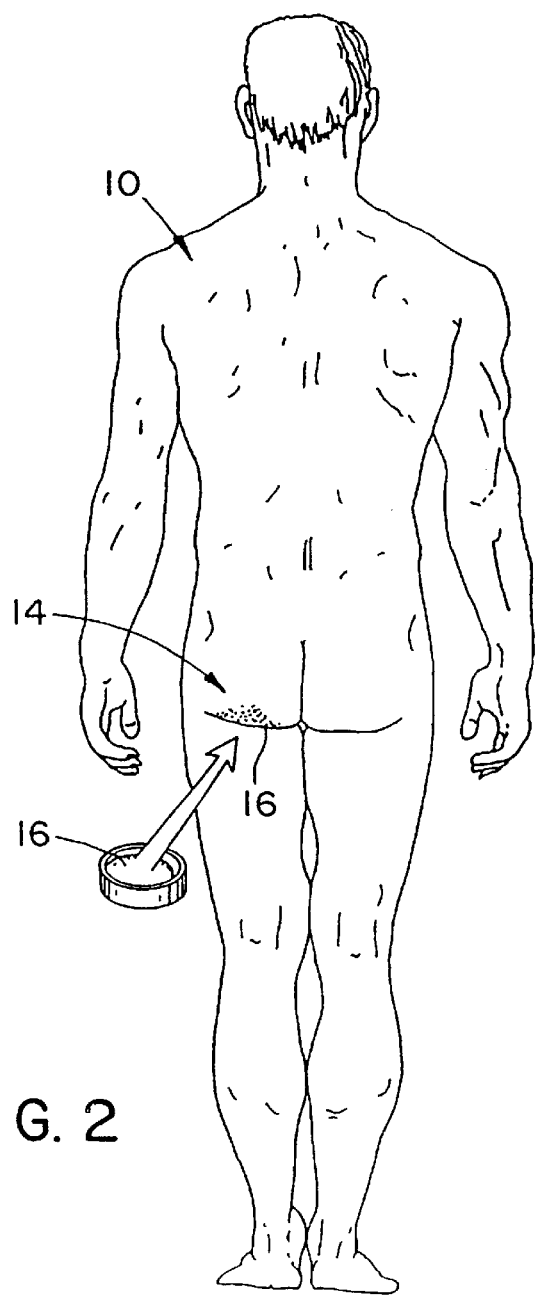

FIG. 2 illustrates the same patient 10 with an inflamed area 14 with an opioid, such as morphine sulfate, applied topically in either a gel or a cream.

As a specific example, 90 mg of morphine sulfate may be mixed with 120 cc of a topical gel such as K-Y gel. Again the morphine sulfate is initially provided in solution as 10 mg/cc and with the resultant mixture 16 comprising 90 mg of morphine sulfate in a total of 129 cc. The resultant set or cream is applied to the inflamed area 14 whereby 2 to 3 mg of morphine sulfate covers an area of approximately 6×6 square inches.

DETAILED DESCRIPTION OF THE INVENTION

Although there was a body of studies determining that opioid receptors were found in various peripheral tissues and that peripheral opioid effects would be more pronounced in inflamed than in non-inflamed tissues, there was no specific determination of how to provide an analgesic effect, using narcotics such as morphine, other than by injection of morphine into a closed space such as a joint. The present invention is directed to a method and apparatus for a topical application of an opioid drug, such as morphine, for a direct activation of the peripheral opioid receptors on the surface of the skin, especially human skin, without any substantial transdermal transmission of the opioid.

The fact that the opioid effects are more pronounced in inflamed than in non-inflamed tissues is a considerable advantage considering that most painful conditions are associated with inflammation, for example, cancer, arthritis, trauma, post-operative pain, skin lesions, etc. It has been determined in the present invention that extremely small systemically inactive doses of both conventional opioid drugs such as morphine, as well as other opioid agents, can produce potent analgesic effects after local application in peripheral tissue.

Initially, it was thought that it would be necessary to inject the morphine into an inflamed area since the inflammation activates the opioid receptors and it was also believed that the morphine had to be in an enclosed space to stay in contact with the area that was inflamed. The initial experiments were conducted in conjunction with arthroscopic surgery of the knee and a number of patients were medicated after arthroscopic surgery with injected morphine. These patients were medicated either with morphine alone, with a local anesthetic such as Marcaine or a combination of Marcaine and 1 mg of morphine. It was shown that patients receiving morphine into the joint had significantly more pain relief than patients receiving the same dose intravenously (demonstrating a local effect) and that this effect was mediated by intraarticular opioid receptors. Furthermore, patients who received just Marcaine after the surgery had relief but the relief typically did not extend beyond 12 hours or at most the next day after surgery. The patients who received Marcaine plus one mg of morphine in the knee had much better relief extending for at least twice as long as those that received Marcaine alone.

At this point, it was still thought that it was necessary to keep the morphine in a closed space, such as in a knee, and the results of such controlled clinical studies reporting analgesia produced by morphine injected into the knee joint were reported in Stein et al., N. Engl. J. Med., 325: 1123–1126 (1991); Comment in N. Engl. J. Med., 325:1168–1169 (1991) and Khoury et al., Anesthes. 77:263–266 (1992). These studies have been replicated by several other groups throughout the world, but this application of morphine was relatively restricted to the practice of orthopedic surgeons using the morphine injected into a joint after arthroscopic surgery and further progress was restricted because it was thought that the morphine had to be contained in the closed space so as to keep the medication in close contact with the inflamed area.

Nevertheless, in the clinical practices of the inventors, while the need for adequate treatment and relief of pain in inflamed skin was evident, there was a lack of evidence that human skin contained peripheral opioid receptors, and there was doubt whether topical administration in the absence of the enclosed conditions akin to administration into the intra-articular space would work. However, based on their laboratory work and in view of the suffering that they hoped to alleviate, the inventors conceived and developed a method of carrying out the concept of effecting topical local analgesia in inflamed skin with opioid agents.

Without wishing to be bound by theory, it is believed that the inflammatory process in peripheral tissue is associated with an increase in sensitivity to the antinociceptive effects of opioid agents, perhaps by activation of opioid receptors located on primary afferent neurons. This may occur by one or more means, e.g., de novo synthesis of opioid receptors which increases the number of receptors; axonal transport of pre-existing receptors to peripheral nerve terminals increasing their concentration and thus sensitivity; some other means of activation of pre-existing neuronal opioid receptors by the inflammatory process. See, e.g., Stein, C., Peripheral and non-neuronal opioid effects. Curr. Opin. Anaesth. 7:347–351 (1994).

Various attempts were made to test the invention. The results are set forth in the Examples and in Tables 1 and 2. In particular, patients for whom various types of inflamed skin conditions, both acute and chronic, were causing intense pain which was not sufficiently alleviated by systemic administration of opioids were treated topically with various formulations of morphine sulfate. Table 1 describes a representative sample of patients treated, and Table 2 describes the results achieved:

TABLE 1

| Patient | Age | Disease | Cause | Pain Medications Before Tx | Description Before Treatment |
| --- | --- | --- | --- | --- | --- |
| 1. | 69 | carcinoma of prostate | radiation therapy | Vicodin Darvocet | Blisters on buttocks with inability to sit for more than a few minutes. |
| 2. | 57 | carcinoma of cervix | radiation therapy | Vicodin Darvocet | Blisters on buttocks with inability to sit for more than a few minutes. |
| 3. | 73 | carcinoma of breast | radiation therapy | Vicodin Darvocet | Very sensitive breasts, whole breasts feel like they are pulling out. Can't sleep on right side. |
| 4. | 4 yr | tonsillectomy | surgery | n/a | unable to swallow for 3–4 days |
| 5. | 6 yr | tonsillectomy | surgery | n/a | unable to swallow for 3–4 days |
| 6. | 13 | third degree hot oil burn on right thigh | burn | none | applying ice on thigh |
| 7. | 28 | second degree sunburn of shoulders | sunburn | none | inability to wear lead apron at work. |
| 8. | 34 | shingles | acute Herpes Zoster | Vicodin × 2 Q 3 hrs | Severe pain. Unable to work, unable to sleep. |
| 9. | 64 | shingles on forehead | acute Herpes Zoster | Vicodin × 2 Q 3 hrs | Severe pain on forehead unrelieved with oral medication. |
| 10. | 81 | shingles of left leg | acute Herpes Zoster | Vicodin × 2 Q 3 hrs | Severe pain left knee, like "on fire". Unable to bend knee. |

TABLE 2

| Patient | Prescription | How many times | Description after Treatment |
| --- | --- | --- | --- |
| 1. | K-Y Jelly Morphine | 120 cc three times 90 mg | no pain at all, able to do bike exercises |
| 2. | K-Y Jelly Morphine | 120 cc every 6 hours 90 cc times 3 days | pain disappears |
| 3. | Saline Morphine | 120 cc every 6 hours 90 cc times 7 days | pain disappeared for six hours; able to sleep all night on right side |
| 4. | Saline Morphine Spray tonsil beds after surgery | 120 cc times one time 90 cc | No pain after surgery; able to swallow and eat ice cream same day |
| 5. | Saline Morphine Spray tonsil beds after surgery | 120 cc times one time 90 cc | No pain after surgery; able to swallow and eat ice cream same day |
| 6. | Saline Morphine | 120 cc spray × 3 90 cc over 3 hours. | Pain is gone; complete healing over two days |
| 7. | Saline Morphine | 120 cc spray × 2 90 cc over 12 hours | Able to wear lead apron immediately. No Rx. needed. |
| 8. | Saline Morphine | 120 cc spray every 4 hours 90 cc times 3 | Stopped all pain medication; healed in three days |
| 9. | K-Y Jelly Morphine | 120 cc every 6 hours 90 cc | 60%–70% of pain disappeared in one day, completely in 3–4 days |

TABLE 2-continued

| Patient | Prescription | How many times | Description after Treatment |
|---|---|---|---|
| 10. | K-Y Jelly | 120 cc every 6 hours | Pain relieved 50% over 3 days; no more pain medication needed. |
| | Morphine | 90 cc | |

The above results were accomplished with the use of only two or three mg of the opioid drug, such as morphine, diluted to be sprayed or applied to a relatively large area of skin such as six inches square and without any side effects such as addiction, dullness in the brain, respiratory depression, nausea, vomiting or itching. All of this was accomplished without any significant absorption of the morphine into the blood stream, since the morphine was merely applied topically to the skin or mucous membranes without any transdermal agent.

In addition to the topical application of the opioid, e.g., morphine, using a spray, the opioid may be applied using a variety of different topical formulations such as gels, creams, etc. Depending upon the particular type of inflammatory skin lesion, the topical application will reduce pain in lesions such as sunburn, dermatitis, psoriasis, burn injuries, radiation burns, skin cancer, herpes simplex (cold sores or genital herpes), herpes zoster (shingles) or after skin grafts. The main advantage is the excellent pain relief without the typical side effects associated with systemically-effective amounts of oral or injectable narcotics which function in the central nervous system. The potential for the present invention is widespread and the topical application opens up a whole new use of narcotics without the prior associated problems.

Figure 1:
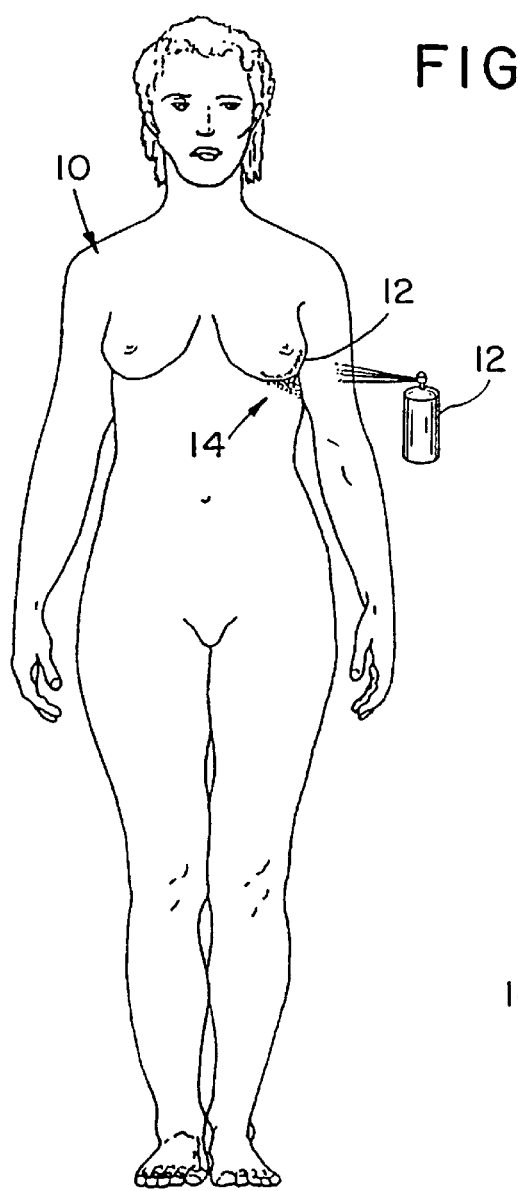
FIG. 1 illustrates a method and apparatus of the present invention and specifically shows a patient 10 receiving a topical application of an opioid drug, such as morphine sulfate, using a spray 12. In particular, a small quantity of the morphine sulfate solution is then sprayed onto an inflamed area 14 on a patient 10 to provide the particular pain relief described above.

In both methods of application as shown in FIGS. 1 and 2 the relief is substantial and with continued application on a periodic basis to continue this relief without any of the typical side effects such as addiction, nausea, inhibition of breathing, somnolence and dysphoria which would typically result if morphine were received by the brain. The quantities of the applied opioid described above are illustrative only and it is to be appreciated that lesser and greater quantities may be used, which can be routinely optimized by the skilled worker. In general, amounts analgesically equivalent to 1–3 mg morphine sulfate applied to an area of 6 in$^2$, or 0.0012–0.0042 mg/kg of body weight, are preferred. However, any quantity of opioid used in the topical application of the present invention is a small fraction of the typical dosage used in other methods of opioid treatment.

Analgesic Agents: It is to be appreciated that all the present invention has been described primarily with reference to the use of morphine in the form of morphine sulfate. Other opioid analgesic drugs and other forms of morphine may be used to interact with the peripheral opioid receptors which are present in inflamed peripheral tissues in various areas of the body and the invention is not to be limited specifically to morphine or morphine sulfate.

Suitable opioid analgesic agents include compounds which have an analgesic effect through binding to any opioid receptor, e.g., a mu-, delta- or kappa-receptor, whereby antinociceptive properties of the agent are functional at the site of inflammation. Examples of such opioid analgesic agents include, but are not limited to morphine, cyclazocine, piperidine, piperazine, pyrrolidine, morphiceptin, meperidine, trifluadom, benzeneacetamine, diacylacetamide, benzomorphan, alkaloids, peptides, phenantrene and pharmaceutically acceptable salts, pro-drugs or derivatives thereof. Specific examples of compounds contemplated by as suitable in the present invention include, but are not limited to morphine, heroin, hydromorphone, oxymorphone, levophanol, methadone, meperidine, fentanyl, codeine, hydrocodone, oxycodone, propoxyphene, buprenorphine, butorphanol, pentazocine and nalbuphine. As used herein, "pharmaceutically acceptable salts, prodrugs and derivatives" refers to derivatives of the opioid analgesic compounds that are modified by, e.g., making acid or base salts thereof, or by modifying functional groups present on the compounds in such a way that the modifications are cleaved, either in routine manipulation or in vivo, to produce the analgesically active parent compound. Examples include but are not limited to mineral or organic salts of acidic residues such as amines, alkali or organic salts of acidic residues such as carboxylic acids, acetate, formate, sulfate, tartrate and benzoate derivatives, etc. Suitable opioid analgesic agents, including those specifically mentioned above, are also described in Goodman and Gilman: Pharmaceutical Basis of Therapeutics. 9th Edition, McGraw Hill 1995, chapter 28, pp. 521–555.

In addition, of course, other active agents may be included in the pharmaceutical composition as required, e.g., topically-effective anaesthetics such as xylocaine, cocaine, lidocaine, benzocaine, etc., which may provide a more immediate, if less effective in the long run, level of pain relief until the opioid agent becomes fully effective. Other active agents which may be present in the pharmaceutical preparations include, e.g., antibiotics, and especially those agents which may themselves cause pain when applied to the inflamed site due to their inherent properties such as pH.

Topical Excipients: The choice of topical excipient as a vehicle for the analgesic agent, while routine, is an important aspect of the claimed invention. The most important criterion for selecting a suitable topical excipient is that it does not enhance delivery of the analgesic agent to the systemic circulation, e.g., transdermal or transmucosal transmission. For example, in general, it is preferred that the topical excipient, especially for application to inflamed skin, not have substantial occlusive properties, which enhance percutaneous transmission of the opioid analgesic agent. Such occlusive vehicles include hydrocarbon bases such as white petrolatum (e.g., Vaseline); anhydrous absorption bases such as hydrophilic petrolatum and anhydrous lanolin (e.g., Aquaphor); and water-in-oil emulsion bases such as lanolin and cold cream.

More preferred are vehicles which are substantially nonocclusive, and generally include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose, and hydroxypropyl methylcellulose (e.g., K-Y Jelly).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87.

Other additives, e.g., for enhancing the adherent properties of the pharmaceutical preparation to various special skin areas, e.g., the axillar, plantar and palmar skin, and mucosal tissues, e.g., in the mouth, on the throat, on the genitalia, particularly the external female genitalia, can be similarly routinely selected and the preparation adapted to such use by one of ordinary skill in the art.

Other Definitions: By "mucosal tissue" is meant tissue comprising a superficial epithelial membrane which is lubricated by mucus. This includes, inter alia, the lining of the mouth, throat, nose, tympanic membrane, external female genitalia, vagina, urethra, rectum and anus. It does not include the conjunctiva of the eye.

By "directly activate peripheral opioid receptors in the inflamed skin or mucosal tissue, but not sufficient to activate central nervous system opioid receptors" is meant that the analgesic action of the opioid is mediated through interaction with the peripheral opioid receptor, e.g., and not through interaction with CNS receptors. See, e.g., Stein (1993), supra, which sets forth criteria for evaluating peripheral opioid receptor antinociception.

By "substantial absence of" or "does not enhance" transdermal or transmucosal delivery of the opioid analgesic agent is meant that upon the induction of analgesia, less than 25%, preferably less than 10%, more preferably less than 5%, still more preferably 1% and most preferably none of the opioid analgesic agent has passed through the stratum corneum, e.g., into the systemic circulation.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. Ser. No. 08/291,614, filed Aug. 17, 1994, are hereby incorporated by reference.

EXAMPLES

Example 1
Analgesia for Cleaning Infected Skin Around a Colostomy

The first study of a patient using the topical application of an opioid drug, and specifically morphine, in accordance with the present invention occurred with a colostomy patient. Specifically, the patient had a severe infection around the colostomy on the skin and the skin was raw, red and inflamed to the degree that it was very difficult to change the dressing and clean the wound and the skin because of the severe pain involved. The patient was receiving 15 or 30 mg, i.v. morphine and still experienced severe pain during changing of the dressing.

Initially, it was thought that a morphine drip might dull the pain sufficiently so as to allow for a changing of the dressing and cleaning of the wound but this proved ineffective, and the patient continued to report severe pain, and treatment with a topical application of morphine was attempted. A very small quantity of morphine was mixed with Xylocaine and was sprayed on the inflamed infectious area. The patient was not given any i.v. morphine before the changing of the dressing and the patient experienced excellent pain relief without any of the normal side effects of morphine. Because of the topical application of morphine, the nursing personnel were able to clean the wound in a very extensive way with relatively no pain for the patient and this was continued for almost a month in the hospital with daily use of the spray without any side effects and with excellent pain relief.

Example 2
Analgesia for Radiation Therapy Burns

A second use of the topical application of morphine was with a series of patients who had burns from radiation therapy. For example, radiation therapy used for cancer of the breast quite often produces areas that are very sore and tender. Other areas where radiation produces burns are in the buttocks when radiation therapy is used for cancer of the prostate. It was decided therefore to treat these various burns using a topical application of morphine such as via a morphine spray. A series of such patients were treated by using morphine alone diluted with a saline solution and with the morphine sprayed over the inflamed area. A very small amount of morphine such as two or three mg of morphine diluted with the saline was sprayed over the inflamed area.

All of the patients so treated reported excellent relief of pain and with the relief starting within 10–15 minutes of topical application. In addition, the relief lasted for at least 6 to 8 hours and up to 12 hours. This was significant since many of the patients reported that they were able to sleep a full night. This had theretofore been difficult because during sleep the patients would turn onto the burned area and awaken. The same experience was accomplished with patients who had pain on the tongue or in the mouth due to radiation burns.

One patient had severe burns on the buttocks due to prostate cancer and upon application of the spray, the patient had excellent relief of the pain. Prior to this time, the patient could not sit or lay on his back to do exercises because of the radiation burns. After the topical application of the morphine, the patient was able to sit for an hour and a half to do exercises and thereby maintain fitness.

Example 3
Analgesia for Sunburns

After the series of patients who were tested who had radiation burns, other patients were tested who had skin burns from the sun. In these cases, we were able to alleviate the pain with less than one mg of morphine, diluted and sprayed on the shoulder areas.

Example 4
Analgesia for Shingles

Other patients who were helped were those who had acute shingles which would produce excruciating pain on the chest. This pain had not been relieved by any kind of narcotics but with the application of the morphine spray, typically three times a day, the patients reported that the pain had been significantly reduced and they were able to wear their clothing without hypersensitivity. The patients also typically healed faster with the use of the topical spray and, for example, after two or three days of using the spray, the healing process was rapidly advanced without any post-herpetic neuralgia.

Example 5
Analgesia for Postsurgical Pain after Tonsillectomy

The morphine spray in saline was used on the tonsil beds after surgery in children undergoing tonsillectomy. Rather than the previous situation, which was generally the inability to swallow for 34 days, these children reported no pain after surgery and were able to swallow and eat ice cream same day they had surgery.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inducing analgesia in inflamed skin or mucosal tissue, comprising topically administering to a patient in need of such treatment a topically effective amount of an opioid analgesic agent, which amount is systemically ineffective for induction of analgesia, admixed with a pharmaceutically acceptable excipient for topical administration, wherein said opioid is cyclazocine, piperidine, piperazine, pyrrolidine, morphiceptin, meperidine, trifluadom, benzeneacetamine, diacylacetamide, benzomorphan, hydromorphone, oxymorphone, levophanol, methadone, meperidine, fentanyl, codeine, hydrocodone, oxycodone, propoxyphene, buprenorphine, butorphanol, pentazocine or nalbuphine.

2. A method of claim 1, whereby effective analgesia in the inflamed skin or mucosal tissue is induced in the substantial absence of transdermal or transmucosal delivery of the opioid analgesic agent.

3. A method of claim 1, wherein the opioid.analgesic agent is administered in an amount analgesically equivalent to up to 3 mg of morphine per 6 $in^2$ of skin.

4. A method of claim 1, wherein the excipient is a liquid and the admixture is administered by spraying the liquid onto the skin or mucosal tissue.

5. A method of claim 1, wherein the excipient is a gel or cream and the admixture is administered by spreading the gel or cream on the skin or mucosal tissue.

6. A method of claim 5, wherein the amount administered is analgesically equivalent to 2–3 mg of morphine.

7. A pharmaceutical composition comprising an admixture of an opioid analgesic agent and a pharmaceutically acceptable excipient for topical administration to inflamed skin or mucosal tissue, wherein a unit dosage amount of the admixture contains a systemically ineffective amount of the opioid analgesic agent, and the excipient does not enhance transdermal or transmucosal transmission of the opioid analgesic agent, with the proviso that, when the admixture is a liquid, it further comprises a component that is pharmaceutically unacceptable for parenteral administration, wherein said opioid is cyclazocine, piperidine, piperazine, pyrrolidine, morphiceptin, meperidine, trifluadom, benzeneacetamine, diacylacetamide, benzomorphan, hydromorphone, oxymorphone, levophanol, methadone, meperidine, fentanyl, codeine, hydrocodone, oxycodone, propoxyphene, buprenorphine, butorphanol, pentazocine or nalbuphine.

8. A pharmaceutical composition of claim 7, wherein a unit dosage amount of the opioid analgesic agent is analgesically equivalent to up to 3 mg of morphine per 6 $in^2$ of skin.

9. A pharmaceutical composition of claim 7, wherein the excipient is a liquid and the admixture is administered by spraying the liquid onto the skin or mucosal tissue.

10. A pharmaceutical composition of claim 7, wherein the excipient is a gel or cream and the admixture is administered by spreading the gel or cream on the skin or mucosal tissue.

11. A pharmaceutical composition of claim 7, in a unit dosage form analgesically equivalent to 2–3 mg of morphine.

12. A pharmaceutical composition comprising an admixture of an opioid analgesic agent and a pharmaceutically acceptable excipient for topical administration, wherein the excipient does not enhance transdermal or transmucosal transmission of the opioid analgesic agent, in a unit dosage form analgesically equivalent to 2–3 mg. of morphine but systemically analgesically ineffective, wherein said opioid is cyclazocine, piperidine, piperazine, pyrrolidine, morphiceptin, meperidine, trifluadom, benzeneacetamine, diacylacetamide, benzamorphan, hydromorphone, oxymorphone, levophanol, methadone, meperidine, fentanyl, codeine, hydrocodone, oxycodone, propoxyphene, buprenorphine, butorphanol, pentazocine or nalbuphine.

13. A container adapted for spraying a measured amount of a liquid onto skin, and containing a pharmaceutical composition comprising an admixture of an opioid analgesic agent and a pharmaceutically acceptable excipient for topical administration.

14. A method of inducing analgesia in inflamed skin or mucosal tissue, comprising topically administering to a patient in need of such treatment a topically analgesically effective amount of an opioid analgesic agent, admixed with a pharmaceutically acceptable excipient for topical administration, wherein the amount of opioid analgesic agent is sufficient to directly activate peripheral opioid receptors in the inflamed skin or mucosal tissue, but not sufficient to activate central nervous system opioid receptors, wherein said opioid is cyclazocine, piperidine, piperazine, pyrrolidine, morphiceptin, meperidine, trifluadom, benzeneacetamine, diacylacetamide, benzomorphan, hydromorphone, oxymorphone, levophanol, methadone, meperidine, fentanyl, codeine, hydrocodone, oxycodone, propoxyphene, buprenorphine, butorphanol, pentazocine or nalbuphine.

15. A method of claim 14, whereby effective analgesia in the inflamed skin or mucosal tissue is induced in the substantial absence of transdermal or transmucosal delivery of the opioid analgesic agent.

16. A method of claim 14, wherein the opioid analgesic agent is administered in an amount analgesically equivalent to up to 3 mg of morphine per 6 $in^2$ of skin.

17. A method of claim 14, wherein the inflamed skin or mucosal tissue is a herpetic lesion.

18. A method of claim 17, wherein the herpetic lesion is shingles.

19. A method of claim 1, wherein the inflamed skin or mucosal tissue is a herpetic lesion.

20. A method of claim 1, wherein the herpetic lesion is shingles.

* * * * *